(12) United States Patent
Schnetter

(10) Patent No.: US 11,112,469 B2
(45) Date of Patent: Sep. 7, 2021

(54) CONTROL OF A RADIO-FREQUENCY AMPLIFIER OF A MAGNETIC RESONANCE SYSTEM

(71) Applicant: Siemens Healthcare GmbH, Erlangen (DE)

(72) Inventor: Volker Schnetter, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 18 days.

(21) Appl. No.: 16/598,976

(22) Filed: Oct. 10, 2019

(65) Prior Publication Data
US 2020/0116806 A1 Apr. 16, 2020

(30) Foreign Application Priority Data

Oct. 11, 2018 (EP) ..................................... 18199924

(51) Int. Cl.
*G01R 33/28* (2006.01)
*A61B 5/01* (2006.01)
*A61B 5/055* (2006.01)
*G01R 33/36* (2006.01)

(52) U.S. Cl.
CPC .............. *G01R 33/288* (2013.01); *A61B 5/01* (2013.01); *A61B 5/055* (2013.01); *G01R 33/3614* (2013.01)

(58) Field of Classification Search
USPC ......................................................... 324/315
See application file for complete search history.

(56) References Cited

U.S. PATENT DOCUMENTS

| | | |
|---|---|---|
| 2003/0080738 A1 | 5/2003 | Brinker |
| 2010/0327868 A1 | 12/2010 | Gebhardt |
| 2013/0147479 A1 | 6/2013 | Bielmeier |
| 2014/0310224 A1 | 10/2014 | Carluccio |
| 2015/0002147 A1 | 1/2015 | Fontius |
| 2015/0061681 A1 | 3/2015 | Renz |
| 2015/0234019 A1 | 8/2015 | Biber |
| 2017/0307710 A1 | 10/2017 | Boulant |
| 2019/0056465 A1* | 2/2019 | Schnetter ............. G01R 33/288 |

OTHER PUBLICATIONS

Google Translation of European Patent Application No. 18199924.4-1022 dated May 17, 2019. (Year: 2019).*
European Search Report for European Patent Application No. 18199924.4-1022 dated May 17, 2019.
Ghosh, Suvradip, Hsuan-Tsung Wang, and Walter El Leon-Salas. "A circuit for energy harvesting using on-chip solar cells." IEEE Transactions on Power Electronics 29.9 (2013): 4658-4671.

(Continued)

*Primary Examiner* — Rodney E Fuller
(74) *Attorney, Agent, or Firm* — Lempia Summerfield Katz LLC

(57) ABSTRACT

A method for control of a radio-frequency amplifier of a magnetic resonance system is provided. The method includes determining a radio-frequency power to be output by the radio-frequency amplifier during an examination of a patient in the magnetic resonance system. Using a Lambert W function, a maximum temperature in tissue of the patient is determined as a function of the radio-frequency power. The radio-frequency amplifier is set as a function of the maximum temperature.

16 Claims, 6 Drawing Sheets

(56) References Cited

OTHER PUBLICATIONS

ISO: " ISO 14708-3:2017(en): Implants for surgery—Active implantable medical devices—Part 3: Implantable neurostimulators", 2017, https://www.iso.org/obp/ui/#iso:std:iso:14708:-3:ed-2:v1:en.
Murbach, Manuel, et al. "Virtual population-based assessment of the impact of 3 Tesla radiofrequency shimming and hermoregulation on safety and B+ uniformity." Magnetic resonance in medicine 76.3 (2016): 986-997.
Neufeld, Esra, et al. "Rapid method for thermal dose-based safety supervision during MR scans." Bioelectromagnetics 36.5 (2015): 398-407.
Pennes, Harry H. "Analysis of tissue and arterial blood temperatures in the resting human forearm." Journal of applied physiology 1.2 (1948): 93-122.
Simonis, F. F. J. "Assessment of RF heating by MR-based measurements and models". Diss. Utrecht University, 2016. pp. 1-109.

\* cited by examiner

CONTROL OF A RADIO-FREQUENCY AMPLIFIER OF A MAGNETIC RESONANCE SYSTEM

This application claims the benefit of EP 18199924.4, filed on Oct. 11, 2018, which is hereby incorporated by reference in its entirety.

BACKGROUND

The present embodiments relate to controlling a radio-frequency amplifier of a magnetic resonance system.

Magnetic resonance examinations may be used in medical diagnostics. An advantage of the magnetic resonance examination lies in the fact that a patient is not subjected to any radioactive or ionizing radiation during the examination, as the patient would be, for example, during an x-ray examination. However, the patient is subjected to electromagnetic fields during a magnetic resonance examination, which may be absorbed by the tissue of the patient. For creation of magnetic resonance images, a rotating magnetic field (B-field) is created during a magnetic resonance examination, which leads to an induced voltage, whereby currents may flow in the patient. These induced currents and possibly further displacement currents may lead to a heating up of the tissue of the patient. This heating up is to be limited while a magnetic resonance examination is being carried out. What is referred to as the specific absorption rate (SAR) is used as a measure for the absorption of electromagnetic field energy in biological tissue. Various methods in the area of SAR control are described in the publications U.S. Pat. Nos. 6,762,605 B2, 9,625,541 B2, 10,031,193 B2, 9,989,603 B2, 8,547,097 B2, and 9,547,053 B2.

To provide that the patient is protected from an impermissibly high loading with electromagnetic fields and from tissue of the patient becoming too hot during a magnetic resonance examination, the SAR is limited in accordance with standards (e.g., IEC 60601-2-33). In the standard, it is assumed, for example, that a whole body SAR of 4 W/kg increases the body stem temperature by a maximum of 1° C. With transmit coils that do not create a homogeneous B1 field for imaging, the local SAR is to be limited. Corresponding limit values may likewise be defined for this purpose. Recent simulation calculations have shown that, even with a homogeneous B1 field, the local SAR may lie above the value defined in the standard without damaging the tissue of the patient (e.g., higher radiation intensities may be used without damaging the patient).

It can therefore be desirable to determine the damage to tissue more exactly. A possible approach for this is the calculation of the CEM43 value (CEM43: Cumulative Equivalent minutes at 43 Degrees C.), as is described, for example, in the publication "Virtual Population-Based Assessment of the Impact of 3 Tesla Radiofrequency Shimming and Thermoregulation on Safety and B1+ Uniformity," M. Murbach, et al., Magnetic Resonance in Medicine 76:986-997 (2016). This is being discussed within the framework of the group IEC TC62 SC62B MT40 (Magnetic resonance equipment for medical diagnosis) and in ISO14708-3:2017(E): Implants for surgery—Active implantable medical devices—part 3: Implantable neurostimulators, with tissue-specific CEM43 limits.

The following derived definition equation from the Arrhenius damage integral may be used as a starting point, for example:

$$CEM43(\tau) = \int_0^\tau R^{Tstart+T(t)-43°\,C} dt \quad (1)$$

In the above-mentioned publication (Murbach et al.) and also in E. Neufeld, et al., "Rapid method for thermal dose-based safety supervision during MR scans," Biomagnetics 2015:10.1002/bem.21919, it is assumed, using this damage integral as its starting point, that the temperature increase in tissue essentially follows a root function if a perfusion model with exponential perfusion increase is assumed. However, this only represents an approximation, which may give rise to an unnecessary limitation of the electromagnetic fields. It may also be necessary to further limit the electromagnetic fields in order still reliably to prevent tissue damage despite the approximation.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a temperature that is reached in tissue as a result of a magnetic resonance examination is determined as exactly as possible to realize an efficient CEM43 monitoring. This monitoring may switch off the system before a limit value is reached in order to prevent damage in tissue of the patient. It is not a matter of an exact spatial temperature distribution, but of a practical assessment of the maximum possible damage at a given pulse energy or SAR sequence.

The present embodiments provide a method for control of a radio-frequency amplifier of a magnetic resonance system. In the method, a radio-frequency power to be output by the radio-frequency amplifier during an examination of a patient in the magnetic resonance system is determined. Using a Lambert W function, a maximum temperature in tissue of the patient is determined as a function of the radio-frequency power. The radio-frequency amplifier is set as a function of the maximum temperature. For example, the radio-frequency amplifier may be switched off when the maximum temperature in tissue is reached, or a power of the radio-frequency amplifier for a pulse energy or an SAR sequence, for example, may be set so that the maximum temperature is not exceeded.

The determination of the maximum temperature by using a Lambert W function enables a more exact calculation of the maximum temperature increase and thus of CEM43 values to be achieved. This enables the performance of the magnetic resonance system to be improved, through which shorter measurement times, better image quality, or more image slices and thus an improved diagnosis may be achieved. This further enables damage to tissue by temperatures that are too high to be reliably avoided.

The maximum temperature may be a local maximum temperature in a section of the patient's tissue. The tissue section may, for example, include a few cubic centimeters (e.g., 1 $cm^3$ to 10 $cm^3$). In this case, a local radio-frequency power to be output by the radio-frequency amplifier in the tissue section during the examination of the patient in the magnetic resonance system may be determined. Depending on this local radio-frequency power, the maximum temperature in the tissue section of the patient is determined using a Lambert W function.

The determination of the maximum temperature in the tissue section using a Lambert W function offers a greater precision compared to approximation formulae, so that additional safety allowances that are necessary with approximation formulae are not required or may at least be far fewer. By comparison with simulation calculations, which need a comparatively long computation time, the determination of the maximum temperature in the tissue section using a Lambert W function is able to be realized in real time in a magnetic resonance system.

The determination of the local maximum temperature may be carried out, for example, as a function of a local parameter for a vasodilation, of a mass of the tissue section, and/or of a thermal guide value as a result of a perfusion in the tissue section. The vessel system, for example, may play a significant role in the regulation of the thermal balance. A thermal conductivity modeling in the tissue through which blood is flowing is known, for example, from the Pennes' bioheat equation (H. H. Pennes; Analysis of tissue and arterial blood temperatures in the resting human forearm; Journal of Applied Physiology, 1:93-122, 1948). In a general form, the Pennes bioheat equation is as follows:

$$c\varrho \frac{\partial T}{\partial t} = \kappa \nabla^2 T - c_b \omega (T - T_b) + \varrho S + M \qquad (2)$$

The computation of the temperature from this equation requires a simulation or a model. Using a Lambert W function enables the local maximum temperature to be computed directly taking into account the thermal conductance coefficient as a result of the perfusion in the local tissue section. Thus, a simple and exact determination of the local maximum temperature is possible.

The local maximum temperature $T_{max}$ may be determined, for example, by using the Lambert W function $W_0$ in accordance with the equation:

$$T_{max} = \frac{\Delta B}{\log(2)} \cdot W_0 \left( \frac{Sm\log(2)}{G_{Perfo}\Delta B} \right). \qquad (3)$$

In this equation, S refers to the local radio-frequency power in the tissue section, ΔB refers to the local parameter for the tissue extension in the tissue section, m refers to the mass of the tissue section, and $G_{Perfo}$ refers to the thermal conductance coefficient as a result of the perfusion in the tissue section.

The present embodiments provide a further method for control of a radio-frequency amplifier of a magnetic resonance system. In the method, a radio-frequency power to be output by the radio-frequency amplifier during an examination of a patient is determined. The curve of a temperature in tissue over time is further determined in the method. The temperature curve includes at least one preceding temperature in the tissue at a preceding point in time and a current temperature in the tissue at a current point in time. The current temperature is determined as a function of the preceding temperature and as a function of the radio-frequency power at the current point in time. The radio-frequency amplifier is set as a function of the temperature curve. The method therefore enables temperature increases to be determined in a simple manner. A CEM43 value may be determined, for example, based on the temperature curve in order to switch off the radio-frequency amplifier during the magnetic resonance examination (e.g., if a limit value for the CEM43 value is exceeded or in order to output a corresponding warning even before the magnetic resonance examination is started).

The temperature curve may include a local temperature curve in a tissue section of the patient. To determine the radio-frequency power to be output by the radio-frequency amplifier, a local radio-frequency power output by the radio-frequency amplifier in the tissue section during the examination of the patient in the magnetic resonance system is determined. The local temperature curve, which includes a preceding temperature in the tissue section at the preceding point in time and a current temperature in the tissue section at the current point in time, may be determined iteratively, as described previously, taking into account the local radio-frequency power.

In the determination of the local temperature curve, one or more of the following parameters may further be taken into account: A local parameter for the vasodilation in the tissue section; a mass of the tissue section; a thermal conductance coefficient as a result of the perfusion in the tissue section; a time difference between the current point in time and the preceding point in time; and a thermal capacitance of the tissue section.

As described above, the vessel system, for example, may play a significant role in the regulation of the thermal balance. The computation of the temperature and thus of the temperature curve from the previously described Pennes' bioheat equation requires a simulation or a model. The iterative determination of the temperature curve over time enables the local temperature curve to be computed taking into account the thermal conductance coefficient resulting from the perfusion in the local tissue section. Thus, a simple and comparatively precise determination of the local temperature is possible.

The current temperature $T_n$ at the current point in time may be determined in accordance with the equation:

$$T_n = T_{n-1} + \frac{\Delta t \cdot G_{Perfo}}{C} \cdot \left( \frac{sm}{G_{Perfo}\Delta B} - 2^{\frac{T_{n-1}}{\Delta B}} T_{n-1} \right) \qquad (4)$$

In this equation, S refers to the local radio-frequency power in the tissue section, ΔB refers to the local parameter for the vasodilation in the tissue section, m refers to the mass of the tissue section, $G_{Perfo}$ refers to the thermal conductance coefficient as a result of the perfusion in the tissue section, $T_{n-1}$ refers to the preceding temperature at the preceding point in time, Δt refers to the time difference between the current point in time and the preceding point in time, and C refers to the thermal capacitance of the tissue section.

The present embodiments also relate to a magnetic resonance system that includes a gradient field system, a radio-frequency antenna, a radio-frequency amplifier, and a control device. The magnetic resonance system may include further components such as, for example, a basic field magnet as well as an operating facility for the magnetic resonance system. The control device serves to control the gradient field system and the radio-frequency amplifier, to receive the measurement signals recorded by the radio-frequency antenna, to evaluate the measurement signals, and to create magnetic resonance data. The magnetic resonance system is configured to determine a radio-frequency power to be output by a radio-frequency amplifier of the magnetic resonance system during an examination of a patient in the magnetic resonance system and to determine a maximum temperature in tissue of the patient as a function of the radio-frequency power using a Lambert W function. Depending on the maximum temperature, the radio-frequency amplifier is set and controlled. The determination of the radio-frequency power to be output by the radio-frequency amplifier, the determination of the maximum temperature in tissue of the patient, and the setting of the radio-frequency amplifier may be carried out, for example, by the control device. The control device may be an electronic control device (e.g., a microprocessor) and may also include corresponding control information (e.g., a control program). The magnetic resonance system is therefore suitable for carrying out the method described above and corresponding embodiments, and thus, also includes the advantages previously described in connection with the method.

One or more of the present embodiments relate to a further magnetic resonance system that includes a gradient field system, a radio-frequency antenna, a radio-frequency amplifier, and a control device. The control device serves to control the gradient field system and the radio-frequency amplifier, to receive the measurement signals recorded by the radio-frequency antenna, to evaluate the measurement signals, and to create magnetic resonance data. The magnetic resonance system is configured to determine a radio-frequency power to be output by a radio-frequency amplifier of the magnetic resonance system during an examination of a patient in the magnetic resonance system and to determine a temperature curve over time in the tissue of the patient. The temperature curve over time includes at least one preceding temperature in the tissue at a preceding point in time and a current temperature in the tissue at a current point in time. The temperature curve may include further temperatures at preceding points in time. The current temperature is determined as a function of the radio-frequency power at the current point in time and as a function of the preceding temperature. The radio-frequency amplifier is controlled and set as a function of the temperature curve. The determination of the radio-frequency power to be output by the radio-frequency amplifier, the iterative determination of the temperature curve, and the setting of the radio-frequency amplifier may be carried out by the control device, for example. The control device may include an electronic control device (e.g., a microprocessor), as well as including corresponding control information (e.g., a control program). The magnetic resonance system is therefore suitable for carrying out the method described above and corresponding embodiment, and thus, also includes the advantages previously described in connection with the method.

A computer program that may be loaded into a memory of a programmable control device of a magnetic resonance system is also provided in accordance with the present embodiments. All or various of the previously described embodiments may be carried out with this computer program when the computer program is running in the programmable control device. In this case, the computer program may need program means (e.g., libraries or auxiliary functions) in order to realize the corresponding embodiments of the method. Expressed differently, a computer program or software, for example, with which one embodiments of the method described above may be carried out, or which carries out this form of embodiment, is provided. The software may involve source code (e.g., C++) that still has to be compiled, translated, and linked. Alternatively, the software may involve source code that only has to be interpreted, or may involve executable software code that only has to be loaded into the corresponding control device in order to be executed.

The present embodiments provide an electronically-readable data medium (e.g., a DVD, a magnetic tape or a USB stick), on which electronically-readable control information (e.g., software), as has been described above, is stored. When this control information is read from the data medium and is stored in a control device, all embodiments of the method described may be carried out.

BRIEF DESCRIPTION OF THE DRAWINGS

FIG. 2 shows a schematic of an electrical equivalent circuit diagram for a heat flow equation in a stable initial state without any radio-frequency power radiated in.

FIG. 3 shows a schematic of an electrical equivalent circuit diagram for a heat flow equation with radio-frequency power radiated in.

DETAILED DESCRIPTION

Figure 1:
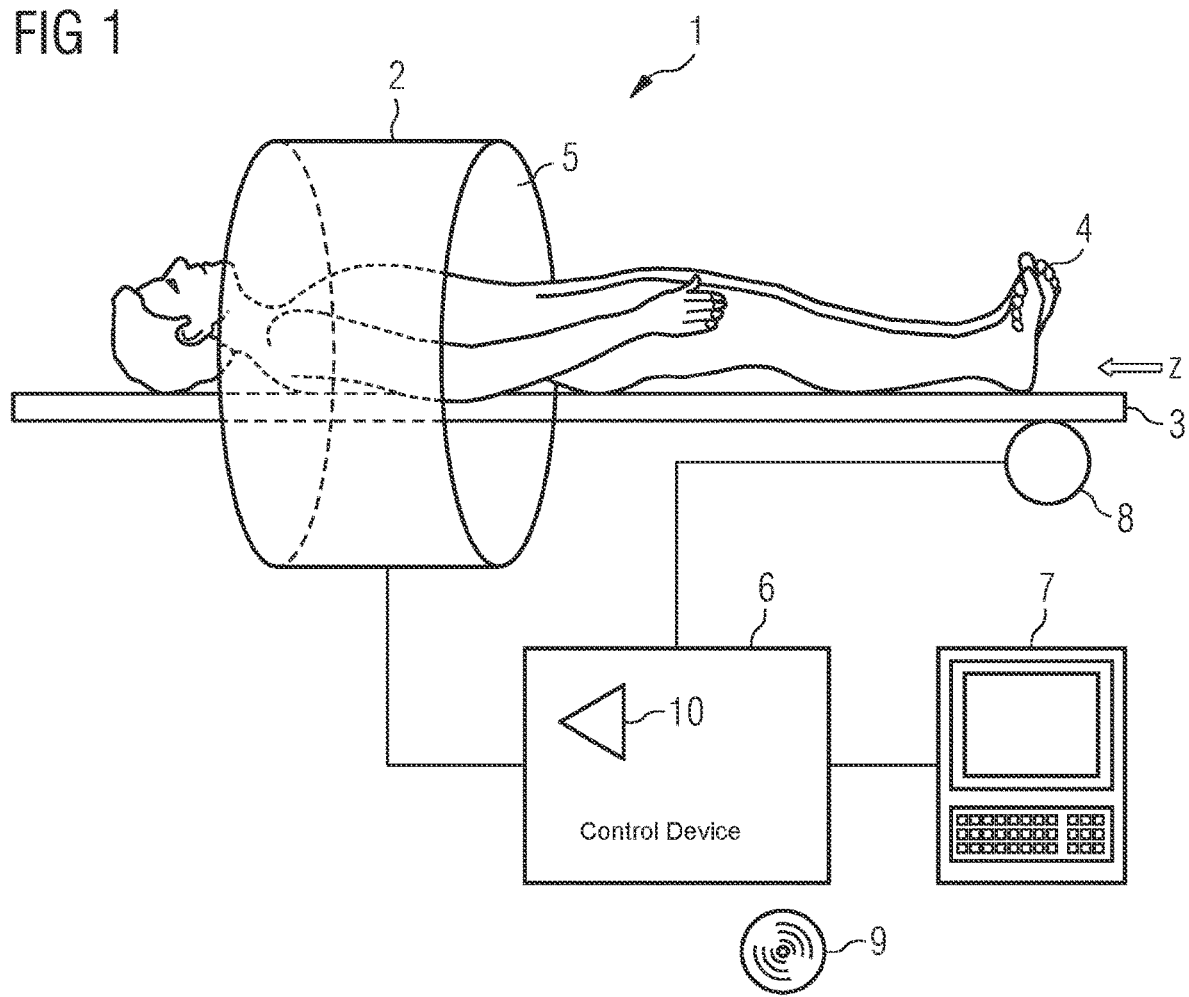
FIG. 1 shows a schematic of one embodiment of a magnetic resonance system.
Figure 13:
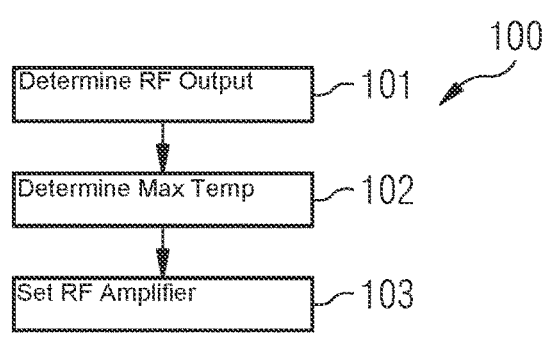
FIG. 13 shows a schematic of one embodiment of a method for avoiding damage to a patient in an examination in a magnetic resonance system.
Figure 14:
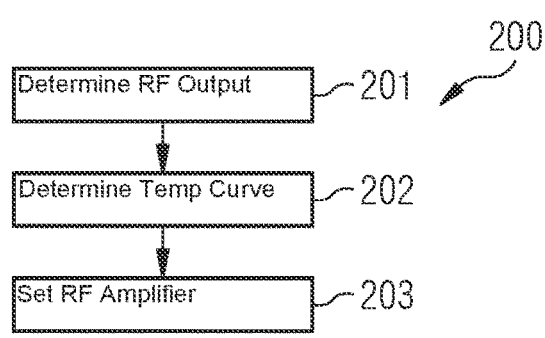
FIG. 14 shows a schematic of a further embodiment of a method for avoiding damage to a patient in an examination in a magnetic resonance system.

FIG. 1 shows a schematic diagram of one embodiment of a magnetic resonance system 1. The magnetic resonance system 1 includes a tomograph 2, an examination table 3 for a person 4 to be examined, who may be moved on the examination table 3 through an opening 5 of the tomograph 2, a control device 6 (e.g., a controller), an evaluation facility 7, and a drive unit 8. The control device 6 controls the tomograph 2 and receives signals that are recorded by the tomograph 2 from the tomograph 2. To create the magnetic resonance data, the tomograph 2 has a basic field magnet, not shown, that creates a basic magnetic field B0, as well as a gradient field system not shown for creation of gradient fields. The tomograph 2 also has one or more radio-frequency antennas for creation of radio-frequency signals and for receiving measurement signals. The one or more radio-frequency antennas are used by the control device 6 and the evaluation facility 7 to create magnetic resonance images. The radio-frequency antennas are activated in this case to generate the radio-frequency signals by a radio-frequency amplifier 10. The radio-frequency amplifier 10 is controlled by the control device 6. The control device 6 also controls the drive unit 8 in order to move the examination table 3 in a direction Z together with the person 4 being examined through the opening 5 of the tomograph 2. The control device 6 and the evaluation facility 7 may include a computer system with a screen, a keyboard, and a data medium 9, on which electronically-readable control information is stored. The electronically-readable control information is configured such that, when the data medium 9 is used in the evaluation facility 7 and the control device 6, the method described with reference to FIGS. 13 and 14 is carried out.

In order to provide that a load on the person being examined (e.g., patient) with electromagnetic fields remains below permitted limits, corresponding limit values may be determined for different regions of the body and modes of operation with a computer program and transferred to an online monitoring unit, which may be configured as part of the control device 6. The online monitoring unit determines the radio-frequency power output by voltage measurement at the radio-frequency amplifier 10, for example. The lost power remaining in the transmit facilities (e.g., radio-frequency antennas) may be subtracted from this. A current specific absorption rate (SAR) may be determined from this using the mass of the patient 4 and compared with the corresponding limit values. If the permitted limit value for the specific absorption rate will be exceeded, then the radio-frequency amplifier 10 is switched off, and thus, the carrying out of the magnetic resonance examination is aborted. With transmit coils that do not create a homogeneous B1 field, the local SAR may be limited.

Simulation computations have shown, however, that even with a homogeneous B1 field, the local SAR may lie above the limit value defined in the standard.

Attempts are therefore being made to determine the damage caused by tissue heating more exactly. A possible approach for doing this is the computation of the CEM43 value (CEM43: Cumulative Equivalent Minutes at 43 Degree Celsius). The CEM43 value may be derived from the damage integral of Arrhenius as:

$$CEM43(\tau) = \int_0^\tau R^{Tstart+T(t)-43°\, C} dt \qquad (5)$$

The global SAR and also the local SAR may be known. To determine the CEM43 value, however, the actual temperature T(t) in tissue is required.

In a general form, this may be determined by the Pennes' bioheat equation:

$$c\varrho \frac{\partial T}{\partial t} = \kappa \nabla^2 T - c_b \omega (T - T_b) + \varrho S + M \qquad (6)$$

with:
c—specific thermal capacitance [Ws/(kgK)]
κ—thermal conductivity [W/(mK)]
ω—perfusion rate [kg/(m³s)]
$\varrho$ —density [kg/m³]
T—temperature [K]
S—SAR [W/kg]

M—metabolic rate per volume unit=Φ/V [W/m³]
Φ—Heat flow [W]
V—Volume [m³]

The index b in this equation refers to parameters that relate to the blood.

The computation of the temperature from the Pennes' bioheat equation (6) requires a simulation or a model.

This equation (6) may be transformed into a heat flow equation and thus makes it possible to observe the power balance:

$$cm \frac{\partial T}{\partial t} = \frac{m}{\varrho} k \nabla^2 T - c_b \omega \frac{m}{\varrho}(T - T_b) + mS + \Phi \qquad (7)$$

The heat flow equation (7) is able to be converted into an analogous electrical equivalent circuit by considering the analogy below.

The temperature T corresponds to the electrical voltage U. The heat flow Φ corresponds to the electrical current I. The thermal resistance R corresponds to the electrical resistance R. The thermal conductance coefficient G corresponds to the electrical conductance coefficient G. The thermal conductivity κ corresponds to the electrical conductivity κ. The thermal capacitance $C_{th}$=cm corresponds to the electrical capacitance C.

The thermal conductance coefficient $G_{cond}$ of the tissue is produced thereafter from the heat flow equation (7) as:

$$G_{cond} = -\frac{m\kappa \nabla^2 T}{\varrho T} \qquad (8)$$

The thermal conductance coefficient $G_{perf}$ through the perfusion of the blood through the tissue is produced from the heat flow equation (7) as:

$$G_{perf} = \frac{c_b \omega m}{\varrho} \qquad (9)$$

Figure 2:
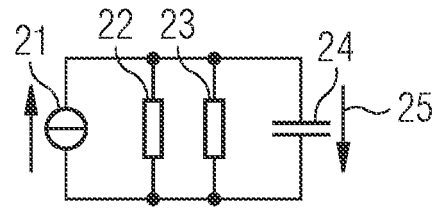

FIG. 2 shows a corresponding electrical equivalent circuit diagram with an electrical power source 21, a first conductance coefficient 22, a second conductance coefficient 23, and a capacitance 24. The electrical power source 21 generates an electrical current I, which corresponds to the thermal heat flow Φ. The first conductance coefficient 22 represents the thermal conductance coefficient $G_{perf}$ through the perfusion of the blood through the tissue, and the second conductance coefficient 23 represents the thermal conductance coefficient $G_{cond}$ of the tissue. The capacitance 24 represents the thermal capacitance $C_{th}$ or the corresponding electrical capacitance C. A voltage U (shown by the voltage arrow 25) across the capacitance 24 thus represents the tissue temperature T.

The following applies for this equivalent electrical circuit diagram shown in FIG. 2:

$$\frac{dU}{dt} = -\frac{G_{perf} + G_{cond}}{C} U + \frac{I}{C} \qquad (10)$$

For the linear case, the solution of this equation is as follows:

$$U(t) = \frac{I(1 - e^{-\frac{t}{\tau}})}{G_{perf} + G_{cond}} + U(t=0)e^{-\frac{t}{\tau}} \text{ with} \tag{11}$$

$$\tau = \frac{c}{G_{perf} + G_{cond}} \tag{12}$$

Starting from a thermally stable state with no radio-frequency power radiated in (e.g., with SAR=0), the tissue has the temperature of the blood. The perfusion of the blood thus has no influence on the temperature, and the basic metabolic rate Φ is so high that the body stem temperature of approximately 36.6° C. is set. It is assumed that the basic metabolic rate remains constant.

This initial state will be disturbed by a magnetic resonance examination. The radio-frequency power radiated in causes an additional flow of heat. The whole-body SAR radiated in leads to an increase in the body stem temperature. In general, a whole-body SAR of 4 W/kg leads to a maximum temperature increase of 1°. This provides that the average factor $m/G_{cond}$ amounts to approximately 0.25 K/(W/kg).

Figure 3:
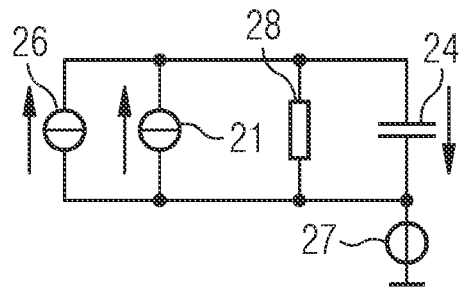

FIG. 3 shows a corresponding electrical equivalent circuit diagram for the case in which a whole-body radio-frequency power of P=SAR*m is radiated in during a magnetic resonance examination. In the equivalent circuit diagram, the whole-body radio-frequency power P is shown as an additional current source 26. A power source 27 is shown in addition in the electrical equivalent circuit diagram of FIG. 3, which represents a temperature deviation from the ambient temperature. When the ambient temperature deviates strongly, the result may be a corresponding balancing reaction of the body, such as, for example, sweating or shivering, through which the conductance coefficient $G_{cond}$ becomes more non-linear. For simplification, the conductance coefficient 28 includes both the thermal conductance coefficient of the tissue and also the thermal conductance coefficient through the perfusion of the blood.

Figure 4:
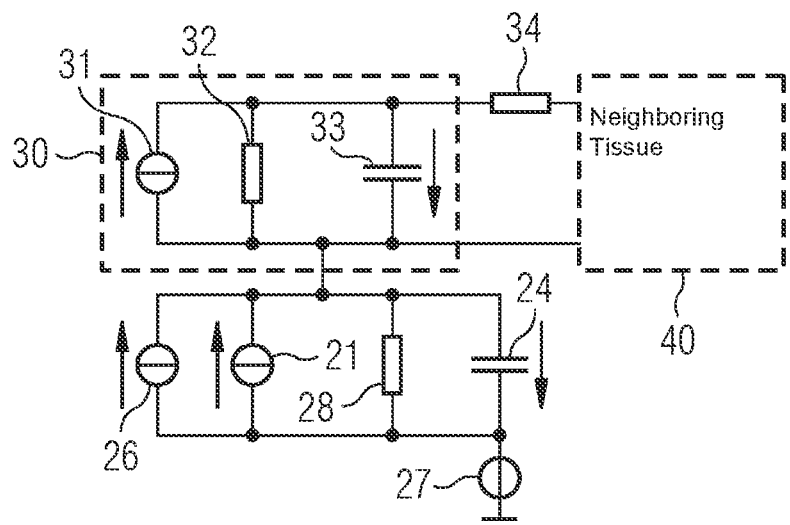
FIG. 4 shows a schematic of an electrical equivalent circuit diagram for a heat flow equation for whole body heating and local heating.

Above and beyond this, a radio-frequency power radiated in locally may be present for a magnetic resonance examination. FIG. 4 shows a corresponding electrical form of embodiment for a local temperature increase in an area 30 with the whole-body radio-frequency power shown previously in conjunction with FIG. 3 (reference characters 21, 24, 26, 27, 28).

In the local area 30, the local SAR has the effect of a radio-frequency power feed, which is represented by the power source 31. The local temperature adjusts to the capacitance 33. In the local area 30, the conductance coefficient 32 acts through the perfusion of the blood. The conductance coefficient 34 represents the thermal conductance coefficient for neighboring tissue 40 in the environment of the local area 30. In the local area 30, a temperature increase $T_{inc}$ is set via the capacitance 33 as a result of the local SAR. Through the heat flow in the neighboring tissue 40, a temperature increase $T_{inc2}$ may likewise occur in the neighboring tissue 40.

Figure 5:
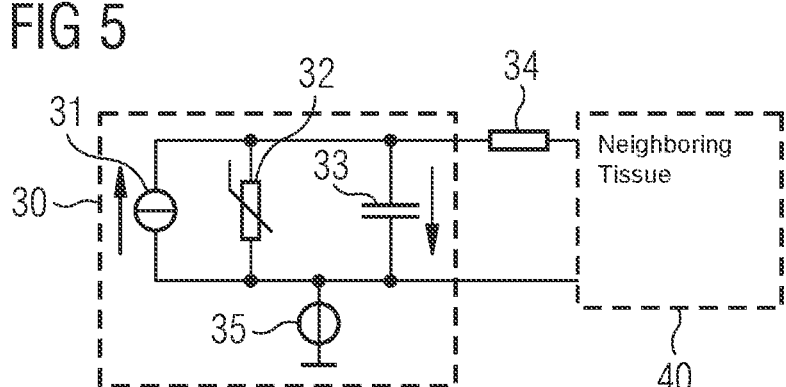
FIG. 5 shows a schematic of an electrical equivalent circuit diagram for a heat flow equation for whole body heating and local heating taking into account a thermoregulation.

For the case in which the local area 30 on which the local SAR acts is located in an area of the environment with the same temperature (e.g., $T_{inc}=T_{inc2}$), a temperature exchange does not take place via the thermal conductivity of the tissue (e.g., conductance coefficient 34). In this case, the thermoregulation may influence the perfusion of the blood, so that the conductance coefficient 32 depends on the temperature $T_{inc}$ and thus becomes more non-linear. FIG. 5 shows a corresponding equivalent circuit diagram for the area 30 with the temperature-dependent conductance coefficient 32. In this case, the power source 35 represents the blood temperature.

For the thermoregulation via the perfusion of the blood, a distinction is to be made between patients with normal thermoregulation and patients with limited thermoregulation, such as, for example, older patients or patients who suffer from diabetes.

Because of the thermoregulation, the perfusion rate ω is dependent on the temperature T. Starting from a perfusion rate $ω_0$ without thermoregulation, the temperature-dependent perfusion rate ω(T) for normal thermoregulation is produced as:

$$ω(T)=ω_0 L_b(T) \tag{13}$$

with the perfusion change $L_b(T)$ for normal thermoregulation. The perfusion change $L_b(T)$ for normal thermoregulation may be described by a local parameter ΔB for the blood vessel dilation as:

$$L_b(T) = 1 \text{ for } T < 37° \text{ C. and} \tag{14}$$

$$L_b(T) = 2^{\frac{T-37}{\Delta B}} \text{ for } T \geq 37° \text{ C.} \tag{15}$$

with ΔB=1.6K and a maximum value for $L_b$ of 32 for skin and a maximum value for $L_b$ of 15 for other tissue.

The temperature-dependent perfusion rate ω(T) for the limited thermoregulation is:

$$ω(T)=ω_0 L_{b\_imp}(T) \tag{16}$$

with the perfusion change $L_{b\_imp}(T)$ for limited thermoregulation. The perfusion change $L_{b\_imp}(T)$ for limited thermoregulation may be described based on the perfusion change $L_b(T)$ for normal thermoregulation as:

$$L_{b\_imp}(T)=1+(0.3(L_b(T)-1))=0.7+0.3L_b(T) \tag{17}$$

with a maximum value for $L_{b\_imp}$ of 10.3 for skin and a maximum value for $L_{b\_imp}$ of 5.2 for other tissue.

Figure 6:
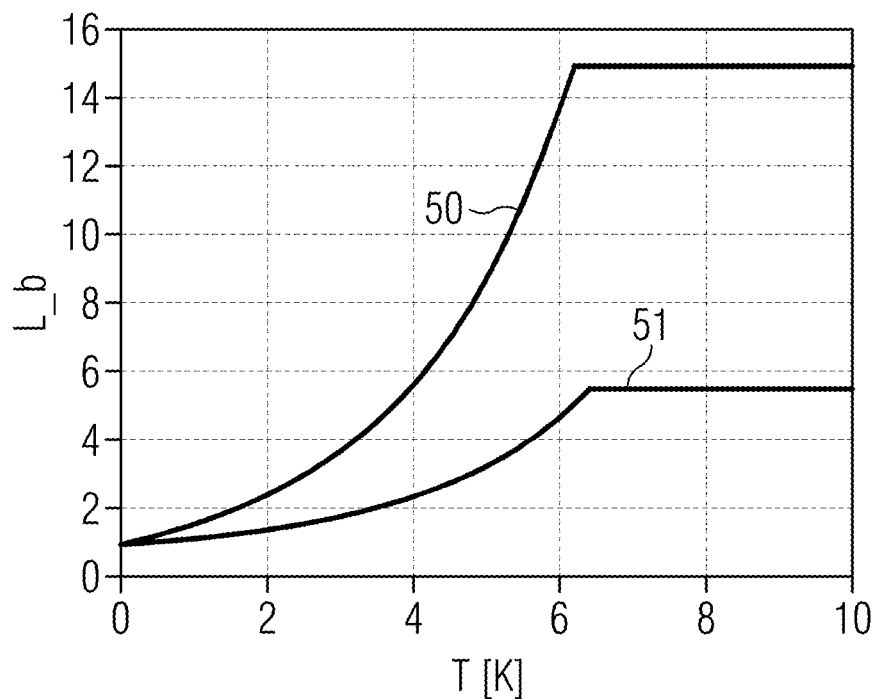
FIG. 6 shows a schematic of a perfusion change for normal thermoregulation and limited thermoregulation.

FIG. 6 shows an example of the course of the perfusion change for other tissue (e.g., not for the skin) for normal thermoregulation with the graph 50 and for the limited thermoregulation with the graph 51.

Figure 7:
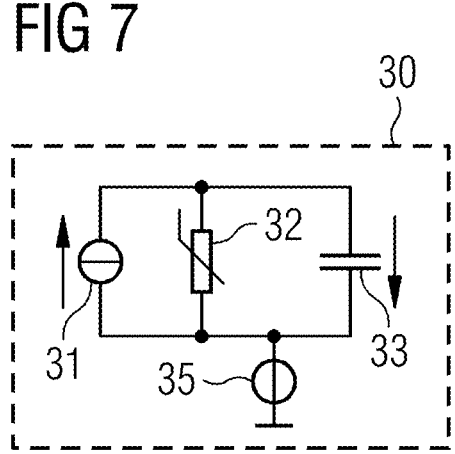
FIG. 7 shows a schematic of an electrical equivalent circuit diagram for a heat flow equation for local heating and local heating taking into account a thermoregulation.

For the electrical equivalent circuit diagram shown in FIG. 7 for the local area 30 (cf., FIG. 5), with the temperature-dependent conductance coefficient 32, the following is thus produced from equation (4):

$$\frac{dU}{dt} = -\frac{G_{perfo} 2^{\frac{U}{\Delta B}}}{C} U + \frac{I}{C} \tag{18}$$

This differential equation is not able to be solved analytically, but may be computed approximately with an approximation method (e.g., a Runge-Kutta method) or be approximated with a function of the form $U_{max}(1-e^{-t/\tau})$.

For a magnetic resonance examination and to protect the patient, it is essentially of interest how high the maximum heating may be and how the heating progresses over time.

A root approximation may be used for determination of the maximum heating, for example. A comparison of this root approximation with the significantly more accurate approximation method according to Runge-Kutta shows, however, that significant inaccuracies may occur, so that, when the root approximation is used, considerable additional allowances for safety are to be made.

FIG. 7, however, shows that the capacitor is charged endlessly to the maximum voltage $I/G_{perf}$ over time. This may be used for determination of the maximum voltage $U_{max}$, which corresponds to the maximum temperature $T_{max}$, as follows. From the equation (18) for the equivalent circuit diagram of FIG. 7, the following is produced:

$$U_{max} = \frac{I}{G_{perfo} 2^{\frac{U}{\Delta B}}} \quad (19)$$

This equation may be transformed to:

$$U_{max} e^{\frac{U_{max}}{\Delta B} \log(2)} = \frac{I}{G_{perfo}} \quad (20)$$

with $$x = \frac{U_{max}}{\Delta B} \log(2)$$

it follows that:

$$xe^x = \frac{I\log(2)}{G_{perfo}\Delta B} \quad (21)$$

A solution of an equation $xe^x = y$ according to x is possible with the aid of a Lambert $W_0$ function: $X = W_0(y)$.

Through back transformation, the following is produced for the maximum electrical voltage $U_{max}$:

$$U_{max} = \frac{\Delta B}{\log(2)} \cdot W_0 \left( \frac{I\log(2)}{G_{Perfo}\Delta B} \right) \quad (22)$$

or for the maximum temperature $T_{max}$ correspondingly:

$$T_{max} = \frac{\Delta B}{\log(2)} \cdot W_0 \left( \frac{Sm\log(2)}{G_{Perf0}\Delta B} \right) \quad (23)$$

The use of the Lambert W function enables the local maximum temperature to be computed directly, taking into account the thermal conductance coefficient as a result of the perfusion in the local tissue section. Thus, a simple and exact determination of the local maximum temperature is possible.

The course of the temperature over time may be computed numerically, for example, as a superposition from heating and cooling. In this case, the root approximation mentioned above may be used as the basis:

$$T_{inc} = d\sqrt{cS} \quad (24)$$

with d=1.3 and c=0.28 K/(W/kg)). With $$\tau = \frac{640s}{1 + \frac{\sqrt{cS}}{d}},$$

there follows the superposition from heating and cooling to:

$$T_n = T_{inc}(1 - e^{\frac{-\Delta t}{\tau}}) + T_{n-1} e^{\frac{-\Delta t}{\tau}} \quad (25)$$

Through approximation of the e function as 1st-order Taylor series with $$e^{\frac{-\Delta t}{\tau}} \cong 1 - \frac{\Delta t}{\tau},$$

there follows:

$$T_n = T_{inc} \frac{\Delta t}{\tau} + T_{n-1} \left(1 - \frac{\Delta t}{\tau}\right) \quad (26)$$

and application of the root approximation:

$$T_n = T_{n-1} + \frac{\Delta t}{\tau} (d\sqrt{cS} - T_{n-1}) \quad (27)$$

A comparison of this estimation of the temperature curve on the basis of the root approximation with the significantly more accurate approximation method according to Runge-Kutter shows, however, that significant inaccuracies may occur, so that, when this estimation is used, considerable additional allowances for safety are to be made.

A significantly more accurate approximation for the local temperature increase may be achieved based on the differential equations for a local area (e.g., the area 30). Starting from the above differential equation (10) for the equivalent circuit diagram shown in FIG. 7, there follows:

$$\frac{dU}{dt} = \frac{I}{C} - \frac{G_{perf0} 2^{\frac{U}{\Delta B}}}{c} U \quad (28)$$

and further by enlargement of the differential d into a Delta $\Delta$:

$$\Delta U = \Delta t \left( \frac{I}{C} - \frac{G_{perf0} 2^{\frac{U}{\Delta B}}}{c} U \right) \quad (29)$$

With the substitution $$\tau_0 = \frac{C}{G_{perf0}},$$

there follows:

$$\Delta U = U_n - U_{n-1} = \Delta t \left( \frac{I}{\tau_0 G_{perf0}} - \frac{2^{\frac{U_{n-1}}{\Delta B}}}{\tau_0} U_{n-1} \right) \quad (30)$$

and from this there follows:

$$U_n = U_{n-1} + \frac{\Delta t}{\tau_0}\left(\frac{I}{G_{perf0}} - 2^{\frac{U_{n-1}}{\Delta B}} U_{n-1}\right) \quad (31)$$

Transformed back from the electrical equivalent circuit into the heat flow, the following is obtained for the temperature $T_n$ at point in time n with ancillary condition $\Delta t/\tau_0 \ll 1$ iteratively from the temperature $T_{n-1}$ at preceding point in time n−1:

$$T_n = T_{n-1} + \frac{\Delta t}{\tau_0}\left(\frac{Sm}{G_{perf0}} - 2^{\frac{U_{n-1}}{\Delta B}} T_{n-1}\right) \quad (32)$$

$\Delta t$ refers to the time difference between the point in time n−1 and the point in time n. The above iterative computing specification is independent of $\tau$.

Figure 8:
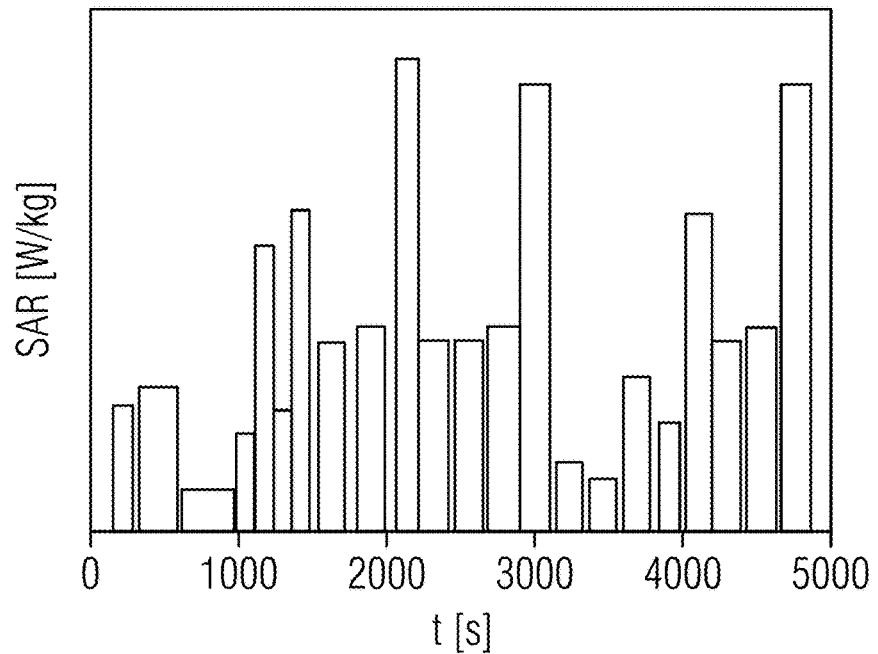
FIG. 8 shows a schematic of a local SAR load over time.

FIG. 8 shows a schematic of a local SAR load over time, as may occur, for example, during a magnetic resonance examination through a radiated-in radio-frequency power in an area of tissue of a patient.

Figure 9:
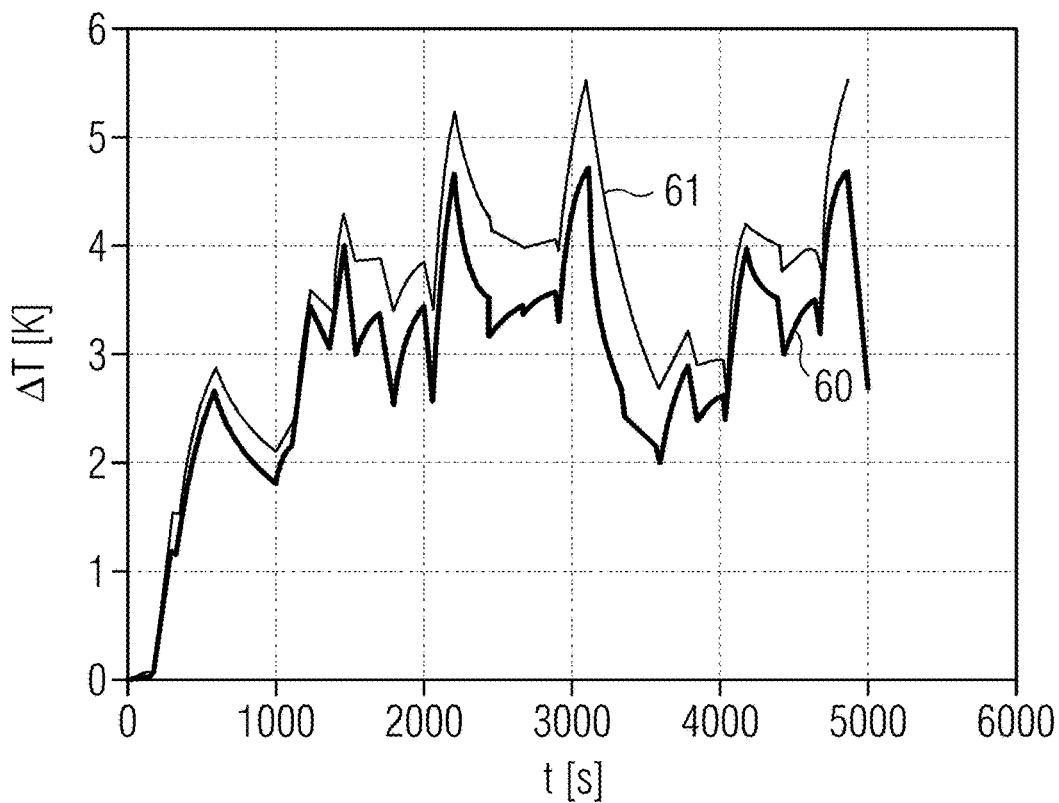
FIG. 9 shows a schematic of a comparison of a rise in temperature with normal thermoregulation in accordance with a Runge-Kutta approximation method, using a root approximation and using an iterative approximation in accordance with an embodiment.

FIG. 9 shows a schematic of a comparison of an increase in temperature as a result of the irradiation shown in FIG. 8 with normal thermoregulation in accordance with a Runge-Kutta approximation method for the equation (18), using the previously described method with root approximation in accordance with equation (27) and using the previously described iterative approximation in accordance with equation (32). The Runge-Kutta approximation method and the approximation in accordance with equation (32) essentially result in the same graph 60 and are therefore not able to be distinguished in the illustration. The method with root approximation in accordance with equation (27) delivers the graph 61. As shown in FIG. 9, the Runge-Kutta method or the approximation in accordance with equation (32) delivers a temperature increase that turns out markedly lower than the temperature increase in accordance with the method with root approximation in accordance with equation (27). This makes possible a more exact calculation of the CEM 43, through which a power advantage in magnetic resonance examinations may be achieved. This manifests itself, for example, in a shorter measurement time, improved image quality, or more image slices, and thus better diagnosability.

Figure 10:
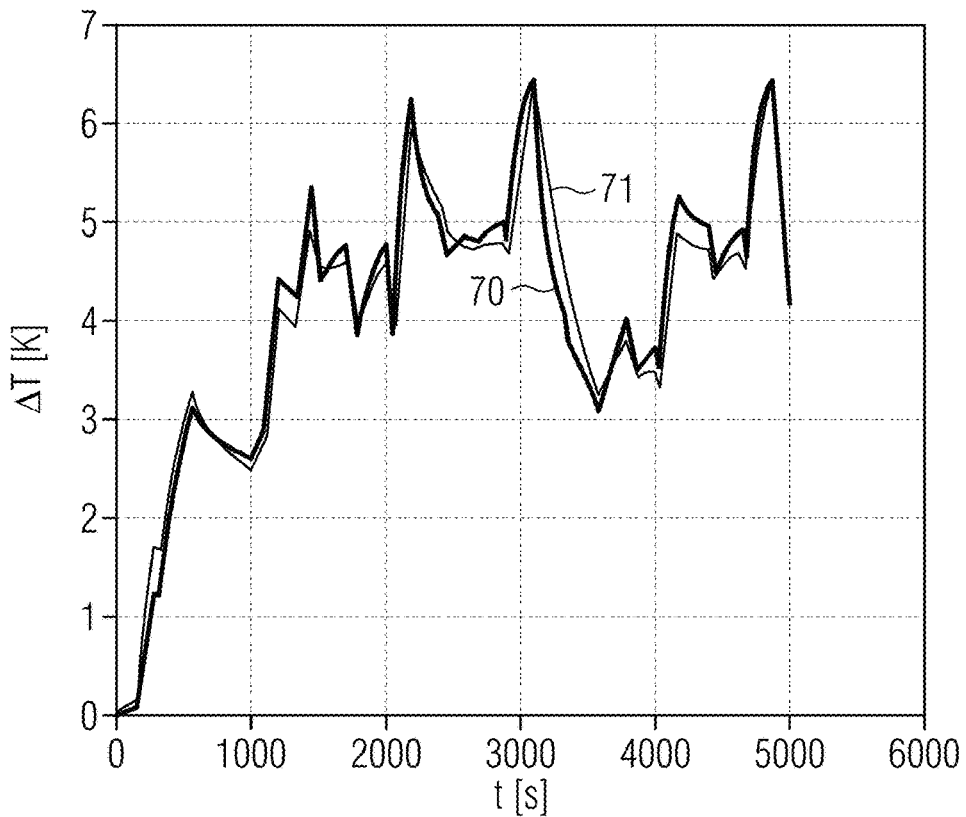
FIG. 10 shows a schematic of a comparison of a rise in temperature with limited thermoregulation in accordance with a Runge-Kutta approximation method, using a root approximation and using an iterative approximation in accordance with an embodiment.

FIG. 10 shows a schematic of a comparison of an increase in temperature with limited thermoregulation in accordance with a Runge-Kutta approximation method for the equation (18), using the previously described method with root approximation in accordance with equation (27) and using the previously described iterative approximation in accordance with equation (32) for irradiation in accordance with FIG. 8. The Runge-Kutta approximation method and the approximation in accordance with equation (32) once again essentially result in the same graph 70. The method with root approximation in accordance with equation (27) delivers the graph 71. As shown in FIG. 10, the temperature increase in accordance with equation (27) (root approximation) does not always lie above the significantly more accurate Runge-Kutta approximation method in accordance with equation (18) or the approximation in accordance with equation (32), so that, for example, for patients with limited thermoregulation, safety precautions are required for the use of the temperature increase in accordance with equation (27) in order to avoid any damage to tissue.

Figure 11:
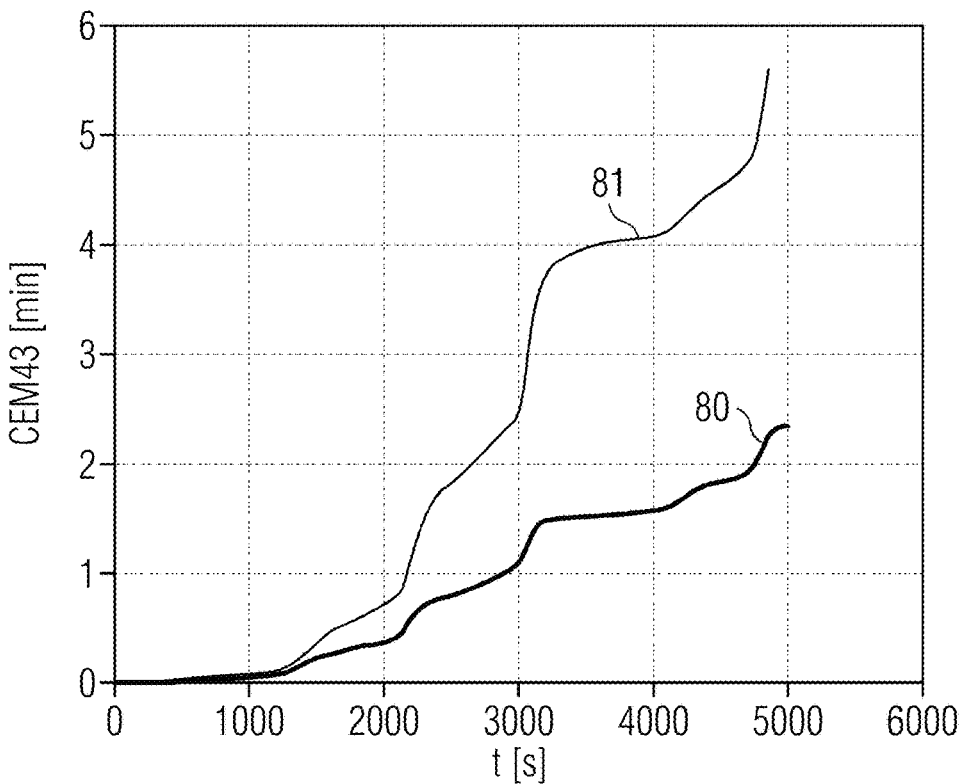
FIG. 11 shows a schematic of a comparison of a CEM43 with normal thermoregulation in accordance with a Runge-Kutta approximation method, using a root approximation and using an iterative approximation in accordance with an embodiment.

FIG. 11 shows a schematic of a comparison of a CEM43 with normal thermoregulation in accordance with the Runge-Kutta approximation method according to equation (18), using the root approximation according to equation (27) and using the iterative approximation according to equation (32). The Runge-Kutta approximation method and the approximation in accordance with equation (32) once again essentially result in the same graph 80. The method with root approximation in accordance with equation (27) delivers the graph 81.

Figure 12:
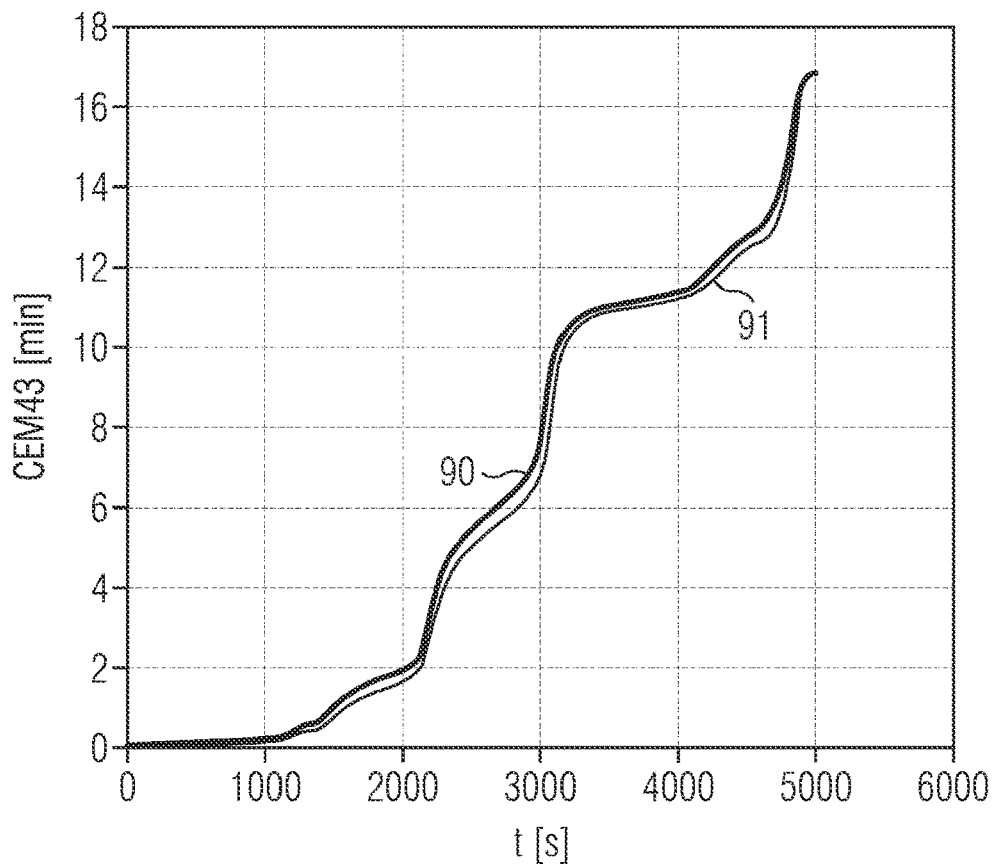
FIG. 12 shows a schematic of a comparison of a CEM43 with restricted thermoregulation in accordance with a Runge-Kutta approximation method, using a root approximation and using an iterative approximation in accordance with an embodiment.

FIG. 12 shows a schematic of a comparison of a CEM43 with limited thermoregulation in accordance with the Runge-Kutta approximation method according to equation (18), using the root approximation according to equation (27) and using the iterative approximation according to equation (32). The Runge-Kutta approximation method and the approximation in accordance with equation (32) once again essentially result in the same graph 90. The method with root approximation in accordance with equation (27) delivers the graph 91.

The previously described method may be carried out by the control device 6 of the magnetic resonance system 1 in advance or during a magnetic resonance examination, for example.

As shown in FIG. 13, the control device 6 may carry out a method 100, for example. In act 101, a radio-frequency power to be output from the radio-frequency amplifier 10 during an examination of the patient 4 in the magnetic resonance system 1 is determined. In act 102, a maximum temperature $T_{max}$ in tissue of the patient 4 is determined as a function of the radio-frequency power using a Lambert W function according to equation (23), for example. In act 103, the radio-frequency amplifier 10 is set as a function of the maximum temperature $T_{max}$ in order to avoid any damage to tissue, for example.

The control device 6 may further carry out a method 200, as is shown in FIG. 14. In act 201, a radio-frequency power to be output from the radio-frequency amplifier 10 during an examination of the patient 4 in the magnetic resonance system 1 is determined. In act 202, a temperature curve over time in tissue of the patient 4 is determined, which includes at least one preceding temperature $T_{n-1}$ in the tissue at a preceding point in time n−1 and a current temperature $T_n$ in the tissue at a current point in time n. The current temperature $T_n$ is determined as a function of the preceding temperature $T_{n-1}$ and as a function of the radio-frequency power S at the current point in time n. The current temperature $T_n$ may be determined, for example, in accordance with equation (32). In act 203, the radio-frequency amplifier 10 is set as a function of the temperature curve.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for control of a radio-frequency amplifier of a magnetic resonance system, the method comprising:
   determining a radio-frequency power to be output by the radio-frequency amplifier during an examination of a patient in the magnetic resonance system;
   determining a maximum temperature in tissue of the patient as a function of the radio-frequency power using a Lambert W function; and
   setting the radio-frequency amplifier as a function of the determined maximum temperature.

2. The method of claim 1, wherein the maximum temperature is a local maximum temperature in a tissue section of the patient, and
   wherein determining the radio-frequency power to be output by the radio-frequency amplifier comprises determining the radio-frequency power to be output by the radio-frequency amplifier in the tissue section during the examination of the patient in the magnetic resonance system.

3. The method of claim 2, wherein determining the local maximum temperature comprises determining the local maximum temperature as a function of a local parameter for a vasodilation, a mass of the tissue section, a thermal conductance coefficient as a result of a perfusion in the tissue section, or any combination thereof.

4. The method of claim 3, wherein the local maximum temperature $T_{max}$ is determined in accordance with the formula:

$$T_{max} = \frac{\Delta B}{\log(2)} \cdot W_0\left(\frac{Sm\log(2)}{G_{Perf0}\Delta B}\right)$$

with:
   a local radio-frequency power S in the tissue section;
   a local parameter $\Delta B$ for the vasodilation in the tissue section;
   a mass m of the tissue section;
   a thermal conductance coefficient $G_{Perf0}$ as a result of the perfusion in the tissue section; and
   a Lambert W function $W_0$.

5. A method for control of a radio-frequency amplifier of a magnetic resonance system, the method comprising:
   determining a radio-frequency power to be output by the radio-frequency amplifier during an examination of a patient in the magnetic resonance system;
   determining a temperature curve over time in tissue of the patient, the tissue curve comprising at least one preceding temperature in the tissue at a preceding point in time and a current temperature in the tissue at a current point in time, wherein the current temperature is determined as a function of the preceding temperature and as a function of the radio-frequency power at the current point in time; and
   setting the radio-frequency amplifier as a function of the temperature curve.

6. The method of claim 5, wherein the temperature curve is a local temperature curve in a tissue section of the patient, and
   wherein determining the radio-frequency power to be output by the radio-frequency amplifier comprises determining the local radio-frequency power to be output by the radio-frequency amplifier in the tissue section during the examination of the patient in the magnetic resonance system.

7. The method of claim 6, wherein determining the local temperature curve comprises determining the local temperature curve as a function of a local parameter for vasodilation in the tissue section, a mass of the tissue section, a thermal conductance coefficient as a result of perfusion in the tissue section, a time difference between the current point in time and the preceding point in time, a thermal capacitance of the tissue section, or any combination thereof.

8. The method of claim 7, wherein the current temperature $T_n$ at the current point in time is determined in accordance with the formula:

$$T_n = T_{n-1} + \frac{\Delta t \cdot G_{Perf0}}{C} \cdot \left(\frac{Sm}{G_{Perf0}\Delta B} - 2^{\frac{T_{n-1}}{\Delta B}} T_{n-1}\right)$$

with:
   a local radio-frequency power S in the tissue section;
   a local parameter $\Delta B$ for the vasodilation in the tissue section;
   a mass m of the tissue section;
   a thermal conductance coefficient $G_{Perf0}$ as a result of the perfusion in the tissue section;
   a preceding temperature $T_{n-1}$ at the preceding point in time;
   a time difference $\Delta t$ between the current point in time and the preceding point in time; and
   a thermal capacitance C of the tissue section.

9. A magnetic resonance system comprising:
   a gradient field system;
   a radio-frequency antenna;
   a radio-frequency amplifier that is coupled to the radio-frequency antenna for output of a radio-frequency signal; and
   a controller configured to:
      control the gradient field system and the radio-frequency amplifier;
      receive measurement signals recorded by the radio-frequency antenna;
      evaluate the measurement signals;
      create magnetic resonance data,
   wherein the magnetic resonance system is configured to:
      determine a radio-frequency power to be output by the radio-frequency amplifier during an examination of a patient in the magnetic resonance system;
      determine a maximum temperature in tissue of the patient as a function of the radio-frequency power using a Lambert W function; and
      set the radio-frequency amplifier as a function of the maximum temperature.

10. The magnetic resonance system of claim 9, wherein the maximum temperature is a local maximum temperature in a tissue section of the patient, and
   wherein the determination of the radio-frequency power to be output by the radio-frequency amplifier comprises determination of the radio-frequency power to be output by the radio-frequency amplifier in the tissue section during the examination of the patient in the magnetic resonance system.

11. A magnetic resonance system comprising:
a gradient field system;
a radio-frequency antenna;
a radio-frequency amplifier that is coupled to the radio-frequency antenna for output of a radio-frequency signal; and
a controller configured to:
control the gradient field system and the radio-frequency amplifier;
receive measurement signals recorded by the radio-frequency antenna;
evaluate the measurement signals; and
create magnetic resonance data,
wherein the magnetic resonance system is configured to:
determine a radio-frequency power to be output by a radio-frequency amplifier of the magnetic resonance system during an examination of a patient in the magnetic resonance system;
determine a temperature curve over time in tissue of the patient, the temperature curve comprising at least one preceding temperature in the tissue at a preceding point in time and a current temperature in the tissue at a current point in time, wherein the current temperature is determined as a function of the preceding temperature and as a function of the radio-frequency power at the current point in time, and
set the radio-frequency amplifier as a function of the temperature curve.

12. The magnetic resonance system of claim 11, wherein the temperature curve is a local temperature curve in a tissue section of the patient, and
wherein the determination of the radio-frequency power to be output by the radio-frequency amplifier comprises determination of the local radio-frequency power to be output by the radio-frequency amplifier in the tissue section during the examination of the patient in the magnetic resonance system.

13. In a non-transitory computer-readable storage medium that stores instructions executable by a controller of a magnetic resonance system to control a radio-frequency amplifier of the magnetic resonance system, the instructions comprising:

determining a radio-frequency power to be output by the radio-frequency amplifier during an examination of a patient in the magnetic resonance system;
determining a maximum temperature in tissue of the patient as a function of the radio-frequency power using a Lambert W function; and
setting the radio-frequency amplifier as a function of the determined maximum temperature.

14. The non-transitory computer-readable storage medium of claim 13, wherein the maximum temperature is a local maximum temperature in a tissue section of the patient, and
wherein determining the radio-frequency power to be output by the radio-frequency amplifier comprises determining the radio-frequency power to be output by the radio-frequency amplifier in the tissue section during the examination of the patient in the magnetic resonance system.

15. The non-transitory computer-readable storage medium of claim 14, wherein determining the local maximum temperature comprises determining the local maximum temperature as a function of a local parameter for a vasodilation, a mass of the tissue section, a thermal conductance coefficient as a result of a perfusion in the tissue section, or any combination thereof.

16. The non-transitory computer-readable storage medium of claim 15, wherein the local maximum temperature $T_{max}$ is determined in accordance with the formula:

$$T_{max} = \frac{\Delta B}{\log(2)} \cdot W_0\left(\frac{Sm\log(2)}{G_{Perfo}\Delta B}\right)$$

with:
a local radio-frequency power S in the tissue section;
a local parameter $\Delta B$ for the vasodilation in the tissue section;
a mass m of the tissue section;
a thermal conductance coefficient $G_{Perfo}$ as a result of the perfusion in the tissue section; and
a Lambert W function $W_0$.

* * * * *